United States Patent
Smith et al.

(10) Patent No.: US 8,026,278 B2
(45) Date of Patent: Sep. 27, 2011

(54) INHIBITORS OF PYRUVATE KINASE AS THERAPEUTIC AGENTS FOR CANCER

(76) Inventors: Brian R. Smith, Lasalle (CA); Tak-Hang Chan, Montréal (CA); Brian Leyland-Jones, Montréal (CA)

( * ) Notice: Subject to any disclaimer, the term of this patent is extended or adjusted under 35 U.S.C. 154(b) by 687 days.

(21) Appl. No.: 11/915,664

(22) PCT Filed: May 29, 2006

(86) PCT No.: PCT/CA2006/000871
§ 371 (c)(1),
(2), (4) Date: Jul. 11, 2008

(87) PCT Pub. No.: WO2006/125323
PCT Pub. Date: Nov. 30, 2006

(65) Prior Publication Data
US 2008/0311183 A1    Dec. 18, 2008

Related U.S. Application Data

(60) Provisional application No. 60/684,979, filed on May 27, 2005.

(51) Int. Cl.
*A01K 31/215*    (2006.01)

(52) U.S. Cl. .......... 514/529; 514/75; 514/136; 514/143; 514/148

(58) Field of Classification Search .................. None
See application file for complete search history.

(56) References Cited

U.S. PATENT DOCUMENTS

| | | |
|---|---|---|
| 2,719,167 A | 9/1955 | Schmidt et al. |
| 2,956,919 A | 10/1960 | Baker et al. |
| 2003/0087961 A1 | 5/2003 | Ko et al. |
| 2004/0009981 A1* | 1/2004 | Bebbington et al. .......... 514/242 |
| 2004/0198750 A1 | 10/2004 | Green et al. |

OTHER PUBLICATIONS

Guverich, et al. "Dimethyl-3-chloro-1-en-2-ylphosphonate. Part 3. Alkylation of anionic O and C nucleophiles and preparation of 1-alkenyl-2-phosphonates" Phosphorus, sulfur and silicon and related Elements, 1999, vol. 148, pp. 61-78.

Csuk, et al. "Allylphosphonates by heteroanalogous zinc-silver/graphite mediated Dreiding-Schmidt reactions" Journal of Carbohydrate Chemistry, 1999, 18(3), pp. 285-295.

Krawczyk, H. "A convnient route to monodealkylation of diethyl phosphonates" Synthetic Communications, 1997, 27(8), pp. 3151-3161.

Knochel, et al. "Syntheses de dienes-1,4-fonctionnalises par addition de zinciques allyliques fonctionnalises sur des alcynes vrais et leur cyclisation en heterocycles ou carbocycles" J. Organometallic Chemistry, 1985, 309(1-2), pp. 1-23.

Britelli, David "A study of the reaction of 2-haloacyl halides with trialkyl phosphites. Synthesis of (2-substituted acyl) phosphonates" J Organic Chemistry, 1985, 50(11), pp. 1845-1847.

Knochel, et al. "Addition of functionalized allylic bromides to terminal alkynes" Tetrahedron Letters, 1984, 25(14), pp. 1475-1478.

Eigenbrodt, et al. "Double role for pyruvate kinase type M2 in the expansion of phosphometabolite pools found in tumor cells" Crit-Rev-Oncog. 1992; 3(1-2): 91-115.

Schneider, Schulze "Comparison of tumor M2-pyruvate kinase (tumor M2-PK), carcinoembryonic antigen (CEA), carbohydrate antigens CA 19-9 and CA 72-4 in the diagnosis of gastrointestinal cancer" Anticancer Res. Nov.-Dec. 2003;23(6D):5089-93.

Yilmaz, et al. "Comparison of pyruvate kinase variants from breast tumor and normal breast" Archives of Medical Research, vol. 34, (2003) Issue 4, pp. 315-324.

Schneider, et al. "Tumor M2-pyruvate kinase in the follow-up of inoperable lung cancer patients: a pilot study" Cancer Letters, vol. 193 (2004), Issue 1, p. 91-98.

Geschwind, et al. "Direct Intraarterial Injection of a Potent Inhibitor of ATP Production" Cancer Research 62 (2002), 3909-3913.

Ko, et al. "Glucose catabolism in the rabbit VX2 tumor model for liver cancer: characterization and targeting hexokinase" Cancer Lett. Nov. 8, 2001;173(1):83-91.

Sparkes, Dixon "The preparation and properties of bromoacetylphosphonic acid" Biochem. J. (1991) 275 (772-773).

Stubbe, Kenyon "Analogs of phosphoenolpyruvate. Specificity of pyruvate kinase from rabbit muscle", Biochemistry, 10 (1971), 2669-2677.

Garcia-Alles, Erni "Synthesis of phosphoeno/pyruvate (PEP) analogues and evaluation as inhibitors of PEP-utilizing enzymes" Eur. j. biochem., 2002, vol. 269, No. 13, pp. 3226-3236.

Peliska, O'Leary "Sulfuryl transfer catalyzed by pyruvate kinase" Biochemistry (1989);28(4):1604-1161.

Slater, et al. "Studies on Succinate-Tetrazolium Reductase Systems. III. Points of Coupling of Four Different Tetrazolium Salts" Biochim Biophys Acta. Nov. 8, 1963;77:383-93.

* cited by examiner

*Primary Examiner* — Sudhakar Katakam

(74) *Attorney, Agent, or Firm* — Benoît & Côté

(57) ABSTRACT

The present invention relates to compounds for the inhibition of pyruvate kinase and ATP production which are capable of inhibiting cancer cells proliferation.

8 Claims, No Drawings

INHIBITORS OF PYRUVATE KINASE AS THERAPEUTIC AGENTS FOR CANCER

BACKGROUND OF THE INVENTION (a) Field of the Invention

The invention relates to novel inhibitors of pyruvate kinase and ATP production specific for the treatment of cancer, pharmaceutical compositions and methods of treatment of cancer thereof.

(b) Description of Prior Art

Most malignant tumors have much higher glucose uptake and glycolysis rates than noncancerous tissues. This is characteristic for many human tumors (including those of brain, liver, lung, colon, stomach and breast). The higher metabolism of glucose is needed by the tumor cells for ATP production, via the glycolysis pathway resulting in pyruvate and ATP:

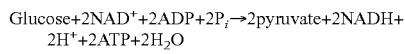

Glucose+2NAD$^+$+2ADP+2P$_i$→2pyruvate+2NADH+ 2H$^+$+2ATP+2H$_2$O

The regulation in the rate of glycolysis is usually achieved by two glycolytic enzymes, one of which is pyruvate kinase (PK). The pyruvate kinase catalyzes the conversion of phosphoenol pyruvate (PEP) to pyruvate with the coupled transfer of the phosphoryl group from PEP to ADP giving ATP:

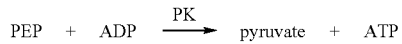

PEP + ADP $\xrightarrow{PK}$ pyruvate + ATP

Several isoforms of pyruvate kinase are known in a tissue-specific manner, such as. L-PK in liver and kidney and M1-PK in brain and muscle. During multi-step carcinogenesis, there is the loss of the tissue-specific isoforms of PK, followed by the expression of the tumor M2-PK (E. Eigenbrodt et al., *Crti. Reve. Oncog.* 3 (1992) 91-115.). Recently the use of the detection of tumor M2-PK as a marker for cancer monitoring, including renal cell carcinoma, gastrointestinal cancer (J. Schneider, G. Schulze, *Anticancer Research*, 23 (2003) 5089-5093), breast cancer (S. Yilmaz, S. Ozan, I. H. Ozercan, *Arch Med Res* 34 (2003) 315-324) and lung cancer (J. Schneider et al., *Cancer Letters*, 193 (2003) 91-98) has been advocated.

Inhibition of ATP production is a plausible strategy for the treatment of cancer. Recently, the use of 3-bromopyruvic acid (3-BrPA) in a direct intraarterial injection to suppress implanted rabbit liver tumors has been reported (J.-F. H. Geschwind et al., *Cancer Research*, 62 (2002) 3909-3913; US patent application published under No. US 2003/0087961 on May 8, 2003). The inhibition of ATP production via inhibition of hexokinase using 3-bromopyruvic acid (3-BrPA) has been suggested (Y. H. Ko et al., *Cancer Letters*, 173 (2001) 83-91), however there is a need for novel inhibitors of ATP production which are more stable and efficacious.

It would be highly desirable to be provided with novel inhibitors of pyruvate kinase and ATP production specific for the treatment of cancer.

SUMMARY OF THE INVENTION

One aim of the present invention is to provide novel inhibitors of pyruvate kinase and ATP production for the treatment of cancer.

In accordance with one embodiment of the present invention there is provided an inhibitor of pyruvate kinase and of ATP production which comprises a compound of formula I:

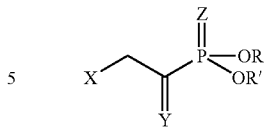

(I)

wherein,

X represents a halide, a sulfonate, an alkoxide, an amineoxide or sulfonium salt, or sulfoxide;

Y represents oxygen, sulphur or CH$_2$;

Z represents oxygen, sulphur or NR;

R and R' represent H, alkyl, aryl or heteroaryl esters;

and any salts thereof.

A preferred inhibitor of the present invention is 2-bromo-1-oxoethylphosphonic acid.

In accordance with another embodiment of the present invention there is provided an inhibitor of pyruvate kinase and of ATP production which comprises a compound of formula II:

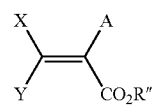

(II)

wherein,

X and Y represent H, halide, or alkyl group;

A is

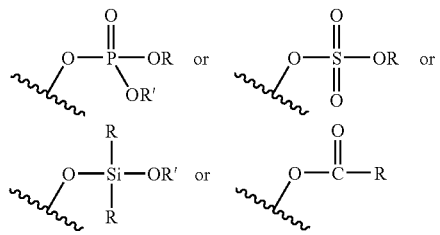

R, R' and R" represent H, alkyl, aryl or heteroaryl esters;

and any salts thereof.

A preferred inhibitor of the present invention comprises a compound of formula III:

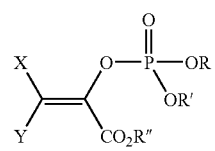

(III)

wherein

X, Y, R R, R' and R" are as defined in claim 3; and any salts thereof.

A preferred inhibitor of the present invention is phosphoenol-3-bromopyruvic acid.

A preferred inhibitor of the present invention, comprises a compound of formula IV:

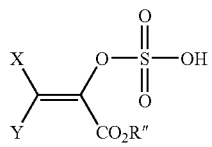

wherein
X, Y, R R, R' and R" are as defined in claim 3; and any salts thereof.

In accordance with another embodiment of the present invention there is provided an inhibitor of pyruvate kinase and of ATP production which comprises a compound of formula V:

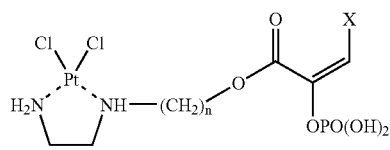

wherein
X represents Cl or Br.

In accordance with another embodiment of the present invention there is provided an inhibitor of pyruvate kinase and of ATP production which comprises a compound of formula VIII:

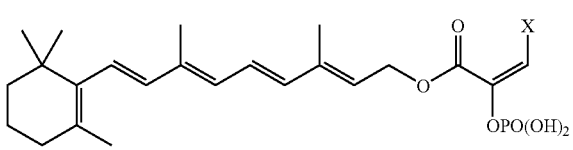

wherein
X represents Cl or Br.

A preferred inhibitor of the present invention comprises a halide selected from the group consisting of: fluoride, bromide, chloride, and iodide.

In accordance with another embodiment of the present invention there is provided a method of treating cancer in a subject comprising administering to the subject an effective amount of an inhibitor of the present invention.

The method may further comprising administering a second chemotherapeutic agent.

The second chemotherapeutic agent may be selected from the group consisting of: altretamine, asparaginase, BCG, bleomycin sulfate, busulfan, carboplatin, carmusine, chlorambucil, cisplatin, claladribine, 2-chlorodeoxyadenosine, cyclophosphamide, cytarabine, dacarbazine imidazole carboxamide, dactinomycin, daunorubicin-dunomycin, dexamethosone, doxurubicin, docetaxol, trastuzumab, etoposide, floxuridine, fluorouracil, fluoxymesterone, flutamide, fludarabine, goserelin, hydroxyurea, idarubicin HCL, ifosfamide, interferon alfa, interferon alfa 2a, interferon alfa 2b, interfereon alfa n3, irinotecan, leucovorin calcium, leuprolide, levamisole, lomustine, inegestrol, melphalan, L-sarcosylin, melphalan hydrochloride, MESNA, mechlorethamine, methotrexate, mitomycin, mitoxantrone, mercaptopurine, paclitaxel, plicamycin, prednisone, procarbazine, streptozocin, tamoxifen, 6-thioguanine, thiotepa, vinblastine, vincristine and vinorelbine tartrate.

The effective amount of the inhibitor may be delivered by direct intraarterial injection or direct intravenous injection to a tumor, or using a delivery system, or administered orally to the patient such as in the form of a tablet, capsule or liquid.

The tumor may be selected from the group consisting of colorectal, glioma, liver, breast, lung or ovarian tumor.

The tumor may be a liver tumor and the inhibitor may be delivered to a hepatic artery.

The inhibitor may be delivered by transcatheteter hepatic artery injection.

The inhibitor or second chemotherapeutic agent may be delivered using a delivery system.

The delivery system may be selected from the group consisting of micelles, liposomes, transdermal and inhalation.

In accordance with another embodiment of the present invention there is provided a composition for treating cancer in a subject comprising an effective amount of an inhibitor of the present invention in association with a pharmaceutically acceptable carrier.

The composition may further comprise a second chemotherapeutic agent.

The second chemotherapeutic agent may be selected from the group consisting of: altretamine, asparaginase, BCG, bleomycin sulfate, busulfan, carboplatin, carmusine, chlorambucil, cisplatin, claladribine, 2-chlorodeoxyadenosine, cyclophosphamide, cytarabine, dacarbazine imidazole carboxamide, dactinomycin, daunorubicin-dunomycin, dexamethosone, doxurubicin, docetaxol, trastuzumab, etoposide, floxuridine, fluorouracil, fluoxymesterone, flutamide, fludarabine, goserelin, hydroxyurea, idarubicin HCL, ifosfamide, interferon alfa, interferon alfa 2a, interferon alfa 2b, interfereon alfa n3, irinotecan, leucovorin calcium, leuprolide, levamisole, lomustine, inegestrol, melphalan, L-sarcosylin, melphalan hydrochloride, MESNA, mechlorethamine, methotrexate, mitomycin, mitoxantrone, mercaptopurine, paclitaxel, plicamycin, prednisone, procarbazine, streptozocin, tamoxifen, 6-thioguanine, thiotepa, vinblastine, vincristine and vinorelbine tartrate.

All publications, patents and patent applications are herein incorporated by reference in their entirety to the same extent as if each individual publication, patent or patent application was specifically and individually indicated to be incorporated by reference in its entirety.

DETAILED DESCRIPTION OF THE INVENTION

In accordance with the present invention, there is provided novel inhibitors of PK and inhibitors of ATP production, novel pharmaceutical compositions and methods of treatment of cancer thereof.

Chemical Synthesis of I,
2-bromo-1-oxoethylphosphonic acid

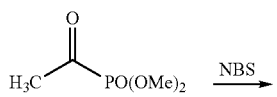

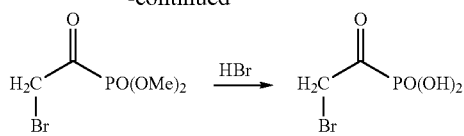

The compound was prepared according to literature procedures (M. J. Sparkes, H. B. F. Dixon, *Biochemical Journal*, 275, 772 (1991)).

The compound was made by brominating dimethyl acetylphosphonate and de-esterifying with HBr.

Chemical Synthesis of III,
phosphoenol-3-bromopyruvic acid as the cyclohexylammonium salt

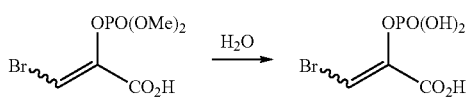

The compound was prepared according to literature procedures (J. A. Stubbe, G. L. Kenyon, *Biochemistry*, 10, 2669 (1971)).

Dimethyl phosphoenol-3-bromopyruvic acid (0.4 g) was dissolved in water (20 ml) and left at room temperature for 0.5 hr. The solvent was then removed in vacuo to give the crude phosphoenol-3-bromopyruvic acid. A solution of cyclohexylamine (0.16 g) in water (10 ml) was then added, and after several minutes, the water was removed in high vacuum. The solid residue was recrystallized from methanol-ether to give cyclohexylammonium dihydrogen phosphoenol-3-bromopyruvate (0.37 g, 73% yield), mp 125-127° (dec.).

Chemical Synthesis of III,
3-chlorophosphoenolpyruvic acid, as the ditriethylammonium salt

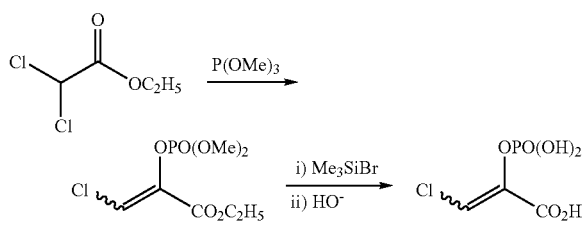

This compound was prepared according to literature procedures (L. F. Carcia-Alles, B. Erni, *Eur. J. Biochem.*, 269, 3226 (2002)).

To trimethyl phosphite (10 mmol) cooled at 0-10° C. was added dropwise ethyl dichloropyruvate (10 mmol). After addition, the ice-bath was removed and the reaction was allowed to proceed at 70° C. for one hour to give the ethyl/ dimethyl ester of 3-chlorophosphoenolpyruvate. It was purified by flash chromatography (hexanes/ethyl acetate, 1:1, v/v) to give 1.5 g (58% yield) of 4:1 mixture of the Z- and E-isomers.

Trimethylsilyl bromide (2 mmol, 0.27 ml) was slowly added to a flask containing the above compound (1 mmol) under argon at 0-4° C. The mixture was stirred for 1 h and then for an additional 1 h at room temperature. After removal of excess trimthylsilyl bromide at high vacuum, cyclohexylamine (2 mmol) in methanol/ether (15 ml) was added. The white solid was collected by filtration and washed with ether to give dicyclohexylammonium ethyl 3-chlorophosphoenolpyruvate (0.30 g, 71% yield).

The above salt (1.2 g, 2.8 mmol) was hydrolysed by the addition of aqueous KOH (1M, 5 mol eq.). The solution was kept at pH 12.5 for 5 h and then neutralized with 1M HCl (final pH value=6.0). The mixture was diluted with deionized water (300 ml) and slowly loaded at 4° C. to a Sephadex DEAE A-25 column (30 g, Cl— form) which was then eluted with a KCl gradient (2 ml/min, 10 ml per fraction, 0.15 M to 0.35 M in 475 min). the compounds were detected at 254 nm. The Z-isomer started to elute at 0.19 M, whereas the E-isomer appeared at 0.27 M KCl. The corresponding fractions were pooled and diluted three times with deionized water. They were loaded on a second Sephadex DEAE A-25 column (HCO₃— form) and eluted with 2 ml/min triethylammonium bicarbonate (02 M to 1 M in 475 min). The fractions containing the product were pooled and lyophilized. Analytical HPLC [DEAE-60-7 column, 1 ml/min, 20 mM $KH_2PO_4$, pH=6.0, KCl (0 mM for 2 min to 360 mM in 16 min)] revealed that the isolated products were more than 99% pure. Retention time for the Z-isomer as ditriethylammonium salt, 13.2 min, 0.47 g, 42% yield; for the E-isomer as ditriethylammonium salt, 16.0 min, 0.11 g, 10% yield.

Chemical Synthesis of IV,
3-chloro-sulfoenolpyruvate, as the potassium salt

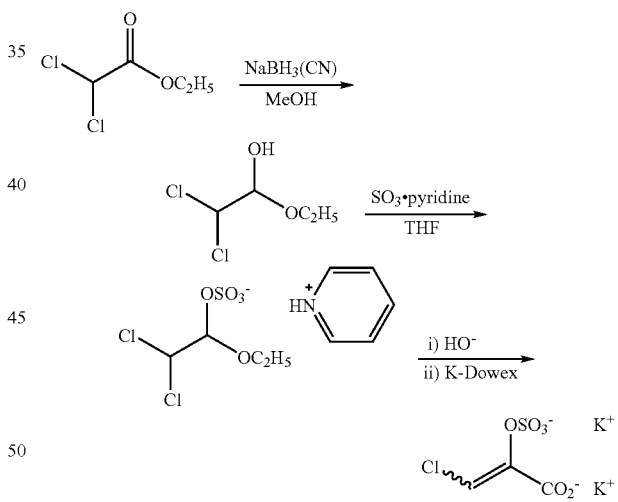

The synthesis was based on a modification of the procedures used for the synthesis of sulfoenolpyruvate (J. A. Peliska, M. H. O'Leary, *Biochemistry*, 28, 1604 (1989)).

Also within the scope of this invention is a pharmaceutical composition that contains an effective amount of one or more of the compounds of this invention and a pharmaceutically acceptable carrier for treating cancer related diseases. Further, the present invention covers a method of administering an effective amount of such a compound to a subject in need of treatment for cancer related diseases. "An effective amount" refers to the amount of the compound which is required to confer a therapeutic effect on the treated subject. An effective amount of the compounds of this invention can range from about 0.001 mg/kg to about 1000 mg/kg. Effective doses will vary, as recognized by those skilled in the art, depending on the diseases treated, route of administration, pharmaceutically acceptable carrier usage, and the possibility of co-usage with other therapeutic treatments such as use of other agents.

The compounds of the invention, as a component of a pharmaceutical composition, can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection direct intravenous injection to a tumor or using a delivery system. The delivery system may be selected from the group consisting of micelles, liposomes, transdermal and inhalation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. For oral administration in a capsule form, useful diluents include lactose and dried corn starch.

The carrier in the pharmaceutical composition is "acceptable" in the sense of being compatible with the active ingredient of the formulation (and preferably, capable of stabilizing it) and not deleterious to the subject to be treated.

In one embodiment the compounds of the invention can be used to treat a tumor which may be selected from but not limited to the group consisting of colorectal, glioma, liver, breast, lung or ovarian tumor.

The tumor may be a liver tumor and the inhibitor may be delivered to a hepatic artery. The inhibitor may be delivered by transcatheteter hepatic artery injection.

The composition may further comprise a second chemotherapeutic agent. The second chemotherapeutic agent may be selected from the group consisting of: altretamine, asparaginase, BCG, bleomycin sulfate, busulfan, carboplatin, carmusine, chlorambucil, cisplatin, claladribine, 2-chlorodeoxyadenosine, cyclophosphamide, cytarabine, dacarbazine imidazole carboxamide, dactinomycin, daunorubicin-dunomycin, dexamethosone, doxurubicin, docetaxol, trastuzumab, etoposide, floxuridine, fluorouracil, fluoxymesterone, flutamide, fludarabine, goserelin, hydroxyurea, idarubicin HCL, ifosfamide, interferon alfa, interferon alfa 2a, interferon alfa 2b, interfereon alfa n3, irinotecan, leucovorin calcium, leuprolide, levamisole, lomustine, inegestrol, melphalan, L-sarcosylin, melphalan hydrochloride, MESNA, mechlorethamine, methotrexate, mitomycin, mitoxantrone, mercaptopurine, paclitaxel, plicamycin, prednisone, procarbazine, streptozocin, tamoxifen, 6-thioguanine, thiotepa, vinblastine, vincristine and vinorelbine tartrate.

The present invention will be more readily understood by referring to the following examples which are given to illustrate the invention rather than to limit its scope.

EXAMPLE 1

Chemical Structures which Bridge PK Inhibitor with Other Bioactive Agents

It is possible to bridge potential PK inhibitor with other bioactive agents through the ester linkage. Within the cancer cell, the ester linkage will be readily hydrolyzed by esterases in the cell to give the active PK inhibitor as well the other bioactive agent. Some possible structures are V and VIII.

For example, compound V can be hydrolyzed by the intracellular esterases to give the PK inhibitor VI and the cis-platin analog VII, both of which can act as cytotoxic agents.

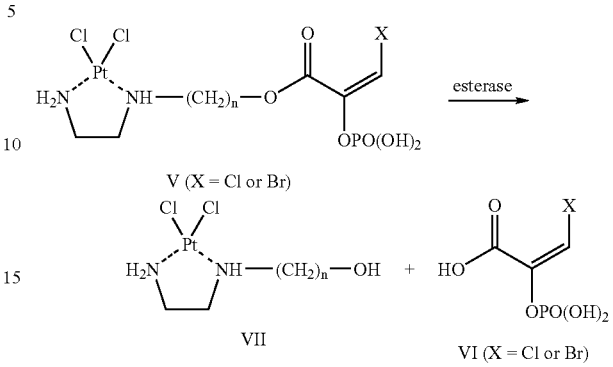

Similarly, compound VIII can be hydrolyzed by esterases to give the PK inhibitor VI and retinol (IX) which can be in situ converted by enzymatic oxidation to retinoic acid (X), a known differentiating agent.

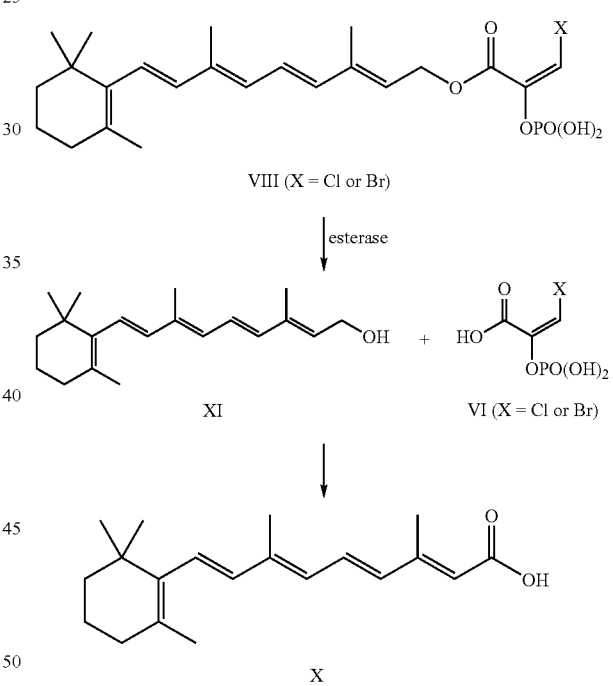

EXAMPLE 2

Additional Details on the Synthesis of I, 2-bromo-1-oxoethylphosphonic acid

All reagents were purchased form Aldrich and used as received unless other-wise stated. 1D, 2D and $^{31}$P NMR were run on a Varian 500 MHz spectrometer.

Step 1 Synthesis of dimethyl acetylphosphonate

Acetyl chloride (7.85 ml, 110 mmol) was cooled to 0° C. and stirred. Trimethylphosphite (11.8 ml, 100 mmol) was added drop-wise over one hour while the cooling was maintained. The mixture was then heated to 80° C. for 5 minute to remove un-reacted acetyl chloride (the flow of argon accelerates the process). The crude product was used in the next step without additional purification (theoretical yield is 15.2 g).
Analytical Data:
$^1$H-NMR (CDCl$_3$, δ, ppm): 2.26 (d, 3H), 3.64 (d, 6H).

Step 2 Synthesis of Dimethyl 2-bromoacetylphosphonate

A few drops of bromine were added to the crude product from Step 1 and the reaction mixture was stirred and slowly warmed until decolourization started (approximately at 50° C.). The remainder of the bromine (2.6 ml, 50 mmol) was added slowly with cooling to keep the temperature below 50° C. We used less than the theoretical quantity of bromine to avoid formation of dibromoacetyl-phosphonate.
Analytical Data:
$^1$H-NMR (CDCl$_3$, δ, ppm): 3.64 (d, 6H), 4.26 (d, 2H)

Step 3 Synthesis of 2-Bromoacetylphosphonic acid

To the crude product from the previous step was added 25 ml of 33% solution of HBr in acetic acid at room temperature. The mixture was kept at room temperature overnight and evaporated under reduced pressure to dryness.
Analytical Data:
$^1$H-NMR (D$_2$O, δ, ppm): 4.68 (br.s)

Step 4 Synthesis of Cyclohexylammonium salt of 2-bromoacetyl-phosphonic acid The crude product from Step 3 was dissolved in 100 ml mixture of water and ice. Cyclohexylamine was added under cooling and stirring in sufficient amount (approx 5 ml) to adjust pH till 3. The solution was again evaporated to dryness, and traces of water were removed by co-evaporation with ethanol. A solid formed which was triturated five times with ethanol and five times with methanol to remove the cyclohexylammonium salts of HBr, acetic acid and acetylphosphonic acid. The solid product was dissolved in methanol (200 ml) and precipitated by the addition of diethyl ether (2 L). The precipitate was filtered and dried to give 3 g of the crude target. This was re-precipitated from a mixture of 150 ml of methanol and 1.5 L of diethyl ether then dried under vacuum for 16 hours giving 2.7 g of pure compound 5 (8.9% overall) as the mono-cyclohexamine salt.
Analytical Data:
$^1$H-NMR (CD$_3$OD, δ, ppm): 4.64 (2H), 3.08 (1H), 1.25-2.04 (10H).
$^{13}$C-NMR (CD$_3$OD, ppm): 25.7, 26.1, 32.1, 39.0, 51.6 (cyclohexylamine), 39.9 (CH$_2$Br), 209.8, 212.1 (C=O).
$^{31}$P-NMR (CD$_3$OD, ppm): −4.77.
MS: m/z 200.9, 202.9 (M-H)$^-$; m/z 121, 123 (M-H—Br); 218.9, 220.9 (M-H+water)
Water content: 3.0% w/w (Karl Fischer).

EXAMPLE 3

Additional Details on the Synthesis of phosphoenol-3-bromopyruvic acid

All reagents were purchased form Aldrich and used as received unless other-wise stated. $^1$H, $^{13}$C, DEPT135, HSQC, HMBC, COSY, 2D and $^{31}$P NMR were run on a Varian 500 MHz spectrometer.

Preparation of 3,3-dibromopyruvic acid

A solution of bromine (15 ml, 46.8 g, 29.3 mmol) in chloroform (100 ml) was prepared. A few drops of this solution were added to a solution of pyruvic acid (11.7 g, 13.3 mmol) in chloroform (100 ml) and stirred until decolorization began (in 10-15 minutes). Then half of the bromine solution was added to the reaction mixture drop-wise with stirring with the rate providing almost complete discoloration of bromine. The remainder of the bromine solution was then added at once. The reaction mixture was heated until boiling and refluxed for 20 hours.

After cooling the reaction mixture to room temperature, white crystals precipitated. The solid was filtered off, washed on filter with chloroform (3×10 ml), dried on air and over P$_2$O$_5$. The mother liquor was concentrated and an additional quantity of the product was obtained. The total yield of the product was 12.8 g (40.2%).
Analytical Data:
$^1$H-NMR (δ, D$_2$O)—5.96 ppm (s, 1H).
Melting point—82-84° C.

Preparation of cyclohexylammonium salt of phosphoenol-3-bromopyruvate

A reaction flask was dried by heating under argon for 5 minutes. After cooling to room temperature it was charged with a solution of trimethyl phosphite (6.2 g, 5.9 ml, 50 mmol) in anhydrous diethyl ether (20 ml). After cooling the reaction mixture with an ice/water bath for 20 minutes, the solution of 3,3-dibromopyruvic acid (9.84 g, 40 mmol) in anhydrous diethyl ether (20 ml) was added at once. Gas evolution began after approximately 2 minutes and continued for several seconds. Then the reaction mixture was allowed to heat to ambient temperature and stirred for an additional 2 hours.
Analytical Data
$^1$H-NMR (δ, D$_2$O): 7.10 ppm (d, 1H); 3.51 ppm (d, 3H); 3.49 ppm (d, 3H)

The reaction mixture was evaporated under reduced pressure until dryness and kept under vacuum for 1 hour to remove the excess trimethylphosphite. The remaining substance was dissolved in water (50 ml) and stirred for 30 minutes. The resulting solution was used further without isolation of 3,3 dibromopyruvic acid.

A solution of cyclohexylamine (4.6 ml, 40 mmol) in water (10 ml) was added to the entire amount of crude reaction mixture (approx. 15 g in 50 ml water) and stirred for 5 minutes. Water was evaporated under vacuum and the solid residue was dried under high vacuum for 1 hour. It was dissolved in methanol (50 ml) and diluted with diethyl ether (500 ml) while stirring. A white precipitate formed. The suspension was stirred overnight, filtered, the solid washed with diethyl ether (100 ml) and air dried to give 900 mg of product. An additional quantity of product was obtained from the mother liquor. Total yield of the product was 1240 mg.

The product was purified by dissolution in water (12.5 ml) at ambient temperature and dilution with acetonitrile (650 ml). The precipitate was filtered off and air dried. Yield of the purified product was 1090 mg. The purified product was washed with acetonitrile (30 ml) by stirring, filtered and air dried. Final yield of cyclohexylammonium dihydrogen phosphoenol-3-bromopyruvate was 870 mg (6.5%).
Analytical Data:
$^1$H-NMR (δ, DMSO-d$_6$): 6.90 ppm (d, 1H), 2.92 ppm (br. m, 1H), 1.07-1.88 ppm (m, 10H);

$^{13}$C-NMR (DMSO-d$_6$, ppm): 23.5, 23.7, 24.6, 30.3, 30.5, 49.3 (all-cyclohexylamine); 105.4 (CHBr), 145.6 [COPO(OH)$_2$], 163.6 (COOH);

$^{31}$P-NMR (CD$_3$OD): −3.65 ppm

MS: m/Z 246.9 (M-1), 244.9 (M-1), 228.9 (M-1-H$_2$O), 226.9 (M-1-H$_2$O), 166.8 (M-Br), 165.0 (M-Br);

Water content: 0.83% w/w (Karl Fisher);

Melting point: 125° C. (dec.).

EXAMPLE 4

Additional Details on the Synthesis of 3-chlorophosphoenolpyruvic acid

Experimental

All reagents were purchased from Aldrich and used as received unless other-wise stated. 1D, 2D and $^{31}$P NMR were run on a Varian 500 MHz spectrometer.

Step 1 Synthesis of ethyl 3,3-dichloropyruvate

A dry 3-neck 500 ml round bottom flask was equipped with a condenser and Ar inlet and outlet. Ethyl pyruvate (48 g, 431 mmol, 1 eq), p-toluenesulfonic acid monohydrate (8 g, 42 mmol) and SO$_2$Cl$_2$ (39 ml) were mixed and refluxed under Ar at 70° C. Additional SO$_2$Cl$_2$ was added in 50 ml aliquots at 4 hour, 6 hour and 22 hour reaction times (total amount of SO$_2$Cl$_2$ 189 ml, 317.5 g, 2.35 mol, 5.5 eq). After reflux for 45 hours, the reaction mixture was allowed to cool to ambient temperature and evaporated on a rotary evaporator at a bath temperature of 50° C. under vacuum. The crude product was mixed with 80 ml of cold water and extracted with diethyl ether (3×50 ml). The ether layer was washed with water (50 ml), brine (50 ml) and dried over anhydrous MgSO$_4$. After filtration, the ether layer was concentrated on a rotary evaporator to get 66.65 g of a yellow oil. The yield of the crude product was 84%. The product was used on the next step without additional purification.

Step 2 Synthesis of ethyl dimethyl 3-chlorophosphoenolpyruvate

A dry 3-neck 250 ml round bottom flask was equipped with a dropping funnel. Trimethylphosphite (53.42 ml, 453 mmol, 1.8 eq) was charged into the flask under an Ar atmosphere and cooled with ice bath to −10° C. Crude Ethyl 3,3-dichloropyruvate (47.72 g, 258 mmol, 1 eq) was added drop wise over 65 minutes. The cooling bath was replaced with oil bath, the mixture was heated at 70° C. for 2 hours. The stirring was continued at ambient temperature for approximately 9 hours. The reaction mixture was concentrated to get 60 g of a yellow oil as crude product. The crude yield was 90%.

Analytical Data:

Z-isomer $^1$H-NMR (δ, D$_2$O, ppm): 6.84 (s, 1H), 4.38-4.28 (q, 2H), 3.97 (s, 3H); 3.94 (s, 3H); 1.39-1.32 (t, 3H).

E-isomer $^1$H-NMR (δ, D$_2$O, ppm): 7.10 (s, 1H), 4.38-4.28 (q, 2H), 3.90 (s, 3H); 3.87 (s, 3H); 1.39-1.32 (t, 3H).

Step 3 Synthesis of ethyl 3-chlorophosphoenolpyruvate dicyclohexyl-ammonium salt The crude product from Step 2 (12.33 g, 47.68 mmol, 1 eq) was added to a dry one neck 100 ml round bottom flask. This was co-evaporated twice with anhydrous ethylacetate (2×40 ml). Anhydrous ethylacetate (40 ml) was then added and the solution cooled to 0° C. Trimethylsilylbromide (20 ml, 150 mmol, 3 eq) was added drop wise over 5 minutes under an Argon atmosphere. The reaction mixture was stirred for an additional 2 hours at 0° C. then allowed to warm to ambient temperature. The excess trimethylsilylbromide was removed by rotary evaporation. A solution of cyclohexylamine (14.92 ml) in a mixture of methanol (145 ml) and diethyl ether (863 ml) was added to the reaction mixture at 0° C. A white precipitate was filtered using a sintered glass filter funnel (Kimax 150 ml-60M) and rinsed with diethyl ether (3×15 ml). During storage of the filtrate a second crop of the product formed. It was collected by filtration and rinsed with diethyl ether. After air drying, 18.92 g (96% yield) of a white solid was obtained.

Analytical Data:

$^1$H-NMR (δ, D$_2$O, ppm): 6.87 (s, 1H, E-isomer), 6.54 (s, 1H, isomer); 4.24-4.13 (q, 2H, E- and Z-isomers); 3.02 (m, 2H); 1.85 (m, 4H); 1.68 (m, 4H); 1.51-1.54 (m, 2H); 1.16-1.24 (m, 11H); 1.04-1.06 (m, 2H).

Step 4 Synthesis of the potassium salt of 3-chlorophosphoenolpyruvic acid

The product from Step 3 (18.8 g, 45.53 mmol, 1 eq) was dissolved in water (20 ml) in a 500 ml round bottom flask and cooled with an ice bath to 0° C. Approximately 182 ml of a 1 M KOH solution was added portion-wise over 5 minutes. The reaction mixture was stirred for an additional 8 hours at ambient temperature and kept in a fridge at 5° C. for approximately 15 hours. The reaction mixture was neutralized with 150 ml of a 1M HCl solution and rotary evaporated at bath temperature of 25° C. This gave 32 g of the wet crude product (containing 1:4 ratio of the two isomers plus phosphoenol pyruvate).

Analytical Data:

$^1$H-NMR (D$_2$O, δ, ppm): 6.79 (s, 1H, E-isomer); 6.30 (s, 1H, Z-izomer).

Separation of E- and Z-isomers of Potassium salt of 3-chlorophosphoenol-pyruvic acid Approximately 3.3 g of crude product from Step 4 was dissolved in 1 L of water and cooled with an ice bath. The cold solution was loaded onto a packed column [column height 65 cm, diameter 2.5 cm, stationary phase approximately 300 ml of sepharose-DEAE (chloride form)] with a flow rate of 2 ml/min. The loaded column was eluted with KCl solution (flow rate 2 ml/min) with linear increasing concentration gradient. The linear gradient was generated by addition of 0.35 M solution of KCl to 250 ml of 0.05 M solution of KCl with rate 2 ml/min. Fractions (10 ml each) were monitored by UV-VIS spectroscopy at 254 nm wavelength. Fractions 73 to 98 contained the 1$^{st}$ isomer while fractions 104 to 124 contained 2$^{nd}$ isomer. The pooled fractions of each isomer were sealed and stored in the fridge.

This procedure was repeated until all the product of Step 4 was chromatographed. The combined fractions from the columns containing the individual isomers were subjected to a second anion-exchange chromatography for transformation to the triethylammonium salt.

Step 5 Synthesis of Triethylammonium salt of Z-3-chlorophosphoenol-pyruvic acid

Approximately 250 ml of the pooled fractions of the potassium salt of the isomer was diluted to 750 ml with water and cooled with ice. It was loaded onto a packed column (column height 65 cm, diameter 2.5 cm, stationary phase ~300 ml of sepharose-DEAE (triethylammonium form)) with a flow rate of 4 ml/min. The loaded column was eluted first with 500 ml of cold water to remove the excess KCl solution then triethylammonium bicarbonate buffer solution with a linear increasing concentration gradient. The linear gradient was generated by the addition of a 1 M solution of triethylammonium bicarbonate at a rate of 4 ml/min into a reservoir containing 500 ml of water. 10 ml fractions were monitored by UV-VIS spectroscopy at 254 nm. Fractions 42 to 72 contained the product. The pooled fractions were stored in the fridge.

The pooled fractions from the columns were combined, rotary evaporated under vacuum at ambient temperature, co-evaporated with methanol to remove excess TEA and co-evaporated with acetonitrile to remove excess water.

Analytical Data:

Z-isomer $^1$H-NMR ($\delta$, $D_2O$, ppm): 7.00 (s, 1H), 3.09-3.15 (q, 18H), 1.18-1.22 (t, 27H) $^{13}$C-NMR ($D_2O$, ppm): 165.6, 141.7, 120.1, 46.7, 8.2

$^{31}$P-NMR ($D_2O$): −4.41 ppm

MS (ESI, negative mode, m/Z): 200.9, 203.0 (M-H).

Water content: 1.72% w/w (Karl Fisher).

E-isomer $^1$H-NMR ($\delta$, $D_2O$, ppm): 6.27 (s, 1H), 3.11-3.16 (q, 18H), 1.19-1.23 (t, 27H) $^{13}$C-NMR ($D_2O$, ppm): 166.1, 142.0, 115.5, 46.6, 8.2

$^{31}$P-NMR ($D_2O$): −3.65 ppm

MS (ESI, negative mode, m/Z): 200.9, 203.0 (M-H).

Water content: 1.41% w/w (Karl Fisher).

EXAMPLE 5

Inhibition of Pyruvate Kinase

The compounds E-3-chlorophosphoenolpyruvate ditriethyl-ammonium salt (ECPDAT), Z-3-chlorophosphoenolpyruvate tritriethyl-ammonium salt (CPTP), phosphoenol-3-bromo-pyruvic acid mono-cyclohexyl ammonium salt (PBPA), 2-bromooxoethylphosphonic acid mono-cyclohexyl-ammonium salt (BOEPA) and 3-bromopyruvic acid (BrPyA) were tested for their efficiency at inhibiting pyruvate kinase. Pyruvate kinase isolated from rabbit muscle was purchased from Sigma-Aldrich. Pyruvate kinase was assayed indirectly by quantifying ADP production formed in the reaction ATP+pyruvate to ADP+phosphoenolpyruvate. Inhibitors were added to the reaction mixture immediately before the reaction was started by the addition of ATP. E-CPDA, CPTP and PBPA inhibited pyruvate kinase at lower concentrations than BrPyA.

TABLE 1

| Compound | Concentration | % Inhibition |
| --- | --- | --- |
| 1 | 10 μM | 100% |
| E-CPDA | 1 μM | 10.9% |
|  | 0.1 μM | 0% |
| 2 | 10 μM | 48.4% |
| CPTP | 1 μM | 43.7% |
|  | 0.1 μM | 0% |
| 3 | 10 μM | 28.6% |
| PBPA | 1 μM | 13.8% |
|  | 0.1 μM | 0% |
| 4 | 10 μM | 0% |
| BOEPA | 1 μM | 0% |
|  | 0.1 μM | 0% |
| 5 | 100 mM | 57.8% |
| BrPyA | 10 mM | 10.9% |
|  | 1 mM | 0% |
|  | 0.1 mM | 0% |

EXAMPLE 6

Inhibition of Cell Proliferation

The compounds of the invention were tested for their inhibition potential of cell proliferation. MCF7 (breast) and SF268 (glioma) cancer cell lines were incubated with different concentrations of the compounds and their viability was assessed using an MTT (3-(4,5-dimethylthiazol-2-yl)-2,5-diphenyltetrazolium bromide) assay. The MTT assay is well known in the art (see for example Slater et al., Biochim. Biophys. Acta 77 (1963) 383). The cells were incubated with a given inhibitor for 72 hours and assayed. As can be seen in table 2, ECPDA, CPTP, PBPA and BOEPA inhibited cell proliferation in both MCF7 and SF268 cells.

TABLE 2

Plate 1: 1: ECPDA MCF7

| ECPDA uM | NC | 0 | 10 | 25 | 50 | 75 | 100 | 200 | 300 | 500 uM |
| --- | --- | --- | --- | --- | --- | --- | --- | --- | --- | --- |
|  | 0.085 | 0.949 | 0.927 | 0.899 | 0.8 | 0.737 | 0.66 | 0.557 | 0.145 | 0.1 |
|  | 0.089 | 0.893 | 0.901 | 0.883 | 0.787 | 0.7 | 0.688 | 0.539 | 0.146 | 0.106 |
|  | 0.087 | 0.868 |  | 0.875 | 0.81 | 0.729 | 0.672 | 0.555 | 0.142 | 0.109 |
|  | 0.081 | 0.894 | 0.902 | 0.86 | 0.774 | 0.735 | 0.673 | 0.925 | 0.166 | 0.117 |
| Average | 0.0855 | 0.901 | 0.91 | 0.8793 | 0.7928 | 0.7253 | 0.6733 | 0.644 | 0.14975 | 0.108 |
| SEM | 0.001708 | 0.0171 | 0.0073655 | 0.0081 | 0.0078 | 0.0086 | 0.0057 | 0.0938 | 0.00548 | 0.003536 |
| A-Blank | 0 | 0.8155 | 0.8245 | 0.7938 | 0.7073 | 0.6398 | 0.5878 | 0.5585 | 0.06425 | 0.0225 |
| % |  | 100 | 101.10362 | 97.333 | 86.726 | 78.449 | 72.072 | 68.486 | 7.8786 | 2.759044 |
| SEM |  | 2.096 | 0.9031833 | 0.9967 | 0.9595 | 1.0529 | 0.7033 | 11.496 | 0.67234 | 0.433542 |

Plate 1: 2: CPTP/MCF7

| CPTP uM | NC | 0 | 10 | 25 | 50 | 75 | 100 | 200 | 300 | 500 |
| --- | --- | --- | --- | --- | --- | --- | --- | --- | --- | --- |
|  | 0.092 | 0.914 | 0.905 | 0.897 | 0.929 | 0.88 | 0.868 | 0.791 | 0.732 | 0.676 |
|  | 0.088 | 0.86 | 0.855 | 0.875 | 0.877 | 0.872 | 0.858 | 0.794 | 0.738 | 0.645 |
|  | 0.067 | 0.853 | 0.849 | 0.853 | 0.879 | 0.823 | 0.844 | 0.761 | 0.737 | 0.634 |
|  | 0.084 | 0.944 | 0.92 | 0.907 | 0.92 | 0.872 | 0.883 | 0.844 | 0.762 | 0.689 |
| Average | 0.08275 | 0.8928 | 0.88225 | 0.883 | 0.9013 | 0.8618 | 0.8633 | 0.7975 | 0.74225 | 0.661 |
| SEM | 0.005498 | 0.0219 | 0.0177735 | 0.012 | 0.0136 | 0.0131 | 0.0082 | 0.0172 | 0.00671 | 0.012891 |
| A-Blank | 0 | 0.81 | 0.7995 | 0.8003 | 0.8185 | 0.779 | 0.7805 | 0.7148 | 0.6595 | 0.57825 |

TABLE 2-continued

| | | | | | | | | | |
|---|---|---|---|---|---|---|---|---|---|
| % | | 100 | 98.703704 | 98.796 | 101.05 | 96.173 | 96.358 | 88.241 | 81.4198 | 71.38889 |
| SEM | | 2.6979 | 2.1942542 | 1.4849 | 1.6734 | 1.6116 | 1.0148 | 2.1231 | 0.82875 | 1.591428 |

Plate 2: 3. PBPA/MCF7

| | | | | | | | | | |
|---|---|---|---|---|---|---|---|---|---|
| PBPA uM | | 0 | 10 | 25 | 50 | 75 | 100 | 200 | 300 | 500 |
| | 0.085 | 0.88 | 0.867 | 0.888 | 0.875 | 0.894 | 0.874 | 0.822 | 0.76 | 0.699 |
| | 0.089 | 0.882 | 0.839 | 0.857 | 0.875 | 0.881 | 0.857 | 0.842 | 0.772 | 0.669 |
| | 0.088 | 0.872 | 0.838 | 0.869 | 0.88 | 0.878 | 0.854 | 0.832 | 0.767 | 0.687 |
| | 0.095 | 0.922 | 0.84 | 0.865 | 0.873 | 0.88 | 0.847 | 0.859 | 0.783 | 0.716 |
| Average | 0.08925 | 0.889 | 0.846 | 0.8698 | 0.8758 | 0.8833 | 0.858 | 0.8388 | 0.7705 | 0.69275 |
| SEM | 0.002097 | 0.0112 | 0.0070119 | 0.0066 | 0.0015 | 0.0036 | 0.0057 | 0.0079 | 0.00484 | 0.009903 |
| A-Blank | 0.0065 | 0.8063 | 0.76325 | 0.787 | 0.793 | 0.8005 | 0.7753 | 0.756 | 0.68775 | 0.61 |
| % | | 99.537 | 94.228395 | 97.16 | 97.901 | 98.827 | 95.71 | 93.333 | 84.9074 | 75.30864 |
| SEM | | 1.384 | 0.865666 | 0.8117 | 0.1843 | 0.449 | 0.7074 | 0.9739 | 0.59742 | 1.22255 |

Plate 2: 4. BOEPA/MCF7

| | | | | | | | | | | |
|---|---|---|---|---|---|---|---|---|---|---|
| BOEPA uM | NC | 0 | 10 | 25 | 50 | 75 | 100 | 200 | 300 | 500 |
| | 0.086 | 0.895 | 0.847 | 0.854 | 0.84 | 0.847 | 0.84 | 0.837 | 0.583 | 0.42 |
| | 0.091 | 0.905 | 0.835 | 0.854 | 0.823 | 0.844 | 0.828 | 0.829 | 0.595 | 0.395 |
| | 0.066 | 0.917 | 0.843 | 0.827 | 0.797 | 0.818 | 0.797 | 0.8 | 0.512 | 0.353 |
| | 0.107 | 0.907 | 0.882 | 0.885 | 0.874 | 0.895 | 0.883 | 0.806 | 0.5 | 0.383 |
| Average | 0.0875 | 0.906 | 0.85175 | 0.855 | 0.8335 | 0.851 | 0.837 | 0.818 | 0.5475 | 0.38775 |
| SEM | 0.008451 | 0.0045 | 0.0103873 | 0.0119 | 0.0161 | 0.016 | 0.0178 | 0.0089 | 0.02421 | 0.013913 |
| A-Blank | 0 | 0.8185 | 0.76425 | 0.7675 | 0.746 | 0.7635 | 0.7495 | 0.7305 | 0.46 | 0.30025 |
| % | | 100 | 93.372022 | 93.769 | 91.142 | 93.28 | 91.57 | 89.249 | 56.2004 | 36.68296 |
| SEM | | 0.5509 | 1.2690644 | 1.4482 | 1.9716 | 1.9605 | 2.1758 | 1.0871 | 2.95775 | 1.699777 |

Plate 4: 1: ECPDA/SF268

| | | | | | | | | | | |
|---|---|---|---|---|---|---|---|---|---|---|
| ECPDA uM | NC | 0 | 10 | 25 | 50 | 75 | 100 | 200 | 300 | 500 |
| | 0.083 | 0.775 | 0.802 | 0.759 | 0.644 | 0.421 | 0.293 | 0.195 | 0.149 | 0.116 |
| | 0.088 | 0.783 | 0.793 | 0.752 | 0.633 | 0.437 | 0.323 | 0.2 | 0.15 | 0.124 |
| | 0.089 | 0.774 | 0.787 | 0.767 | 0.592 | 0.454 | 0.334 | 0.232 | 0.156 | 0.128 |
| Average | 0.095 | 0.803 | 0.777 | 0.78 | 0.644 | 0.478 | 0.361 | 0.216 | 0.16 | 0.131 |
| SEM | 0.001607 | 0.1943 | 2.3015021 | 6.0602 | 12.344 | 18.641 | 24.921 | 49.948 | 74.9621 | 124.9693 |
| A-Blank | 0.01 | 0.698 | 0.672 | 0.675 | 0.539 | 0.373 | 0.256 | 0.111 | 0.055 | 0.026 |
| % | | 83.194 | 80.095352 | 80.453 | 64.243 | 44.458 | 30.513 | 13.23 | 6.55542 | 3.098927 |
| SEM | | 23.164 | 274.31491 | 722.31 | 1471.3 | 2221.8 | 2970.3 | 5953.2 | 8934.69 | 14895.03 |

Plate 4: 2: CPTP/SF268

| | | | | | | | | | | |
|---|---|---|---|---|---|---|---|---|---|---|
| CPTP uM | NC | 0 | 10 | 25 | 50 | 75 | 100 | 200 | 300 | 500 |
| | 0.086 | 0.78 | 0.805 | 0.775 | 0.771 | 0.733 | 0.739 | 0.629 | 0.514 | 0.348 |
| | 0.087 | 0.777 | 0.73 | 0.763 | 0.761 | 0.715 | 0.752 | 0.607 | 0.484 | 0.349 |
| | 0.064 | 0.772 | 0.736 | 0.774 | 0.764 | 0.736 | 0.739 | 0.599 | 0.443 | 0.318 |
| | 0.108 | 0.787 | 0.829 | 0.801 | 0.771 | 0.761 | 0.796 | 0.613 | 0.497 | 0.351 |
| Average | 0.08625 | 0.779 | 0.775 | 0.7783 | 0.7668 | 0.7363 | 0.7565 | 0.612 | 0.4845 | 0.3415 |
| SEM | 0.008985 | 0.0031 | 0.0247689 | 0.0081 | 0.0025 | 0.0095 | 0.0135 | 0.0064 | 0.01514 | 0.007858 |
| A-Blank | 0 | 0.6928 | 0.68875 | 0.692 | 0.6805 | 0.65 | 0.6703 | 0.5258 | 0.39825 | 0.25525 |
| % | | 100 | 99.422591 | 99.892 | 98.232 | 93.829 | 96.752 | 75.893 | 57.4883 | 36.8459 |
| SEM | | 0.4527 | 3.5754503 | 1.1629 | 0.3651 | 1.3661 | 1.9514 | 0.9168 | 2.18484 | 1.134337 |

Plate 5: 3. PBPA/SF268

| | | | | | | | | | | |
|---|---|---|---|---|---|---|---|---|---|---|
| PBPA uM | NC | 0 | 10 | 25 | 50 | 75 | 100 | 200 | 300 | 500 |
| | 0.083 | 0.766 | 0.785 | 0.805 | 0.766 | 0.772 | 0.742 | 0.726 | 0.642 | 0.602 |
| | 0.086 | 0.791 | 0.804 | 0.763 | 0.773 | 0.789 | 0.76 | 0.709 | 0.649 | 0.6 |
| | 0.086 | 0.787 | 0.773 | 0.803 | 0.787 | 0.789 | 0.735 | 0.709 | 0.623 | 0.59 |
| | 0.094 | 0.772 | 0.757 | 0.801 | 0.778 | 0.769 | 0.753 | 0.722 | 0.641 | 0.617 |
| Average | 0.08725 | 0.779 | 0.77975 | 0.793 | 0.776 | 0.7798 | 0.7475 | 0.7165 | 0.63875 | 0.60225 |
| SEM | 0.002358 | 0.006 | 0.0099111 | 0.01 | 0.0044 | 0.0054 | 0.0056 | 0.0044 | 0.00554 | 0.005573 |
| A-Blank | 0.001 | 0.6928 | 0.6935 | 0.7068 | 0.6898 | 0.6935 | 0.6613 | 0.6303 | 0.5525 | 0.516 |
| % | | 100 | 100.10826 | 102.02 | 99.567 | 100.11 | 95.453 | 90.978 | 79.7546 | 74.48575 |
| SEM | | 0.8601 | 1.4306839 | 1.4483 | 0.6374 | 0.776 | 0.8048 | 0.6361 | 0.8002 | 0.804529 |

Plate 5: 4. BOEPA/SF268

| | | | | | | | | | | |
|---|---|---|---|---|---|---|---|---|---|---|
| BOEPA uM | NC | 0 | 10 | 25 | 50 | 75 | 100 | 200 | 300 | 500 |
| | 0.087 | 0.78 | 0.764 | 0.75 | 0.781 | 0.719 | 0.669 | 0.419 | 0.18 | 0.117 |
| | 0.086 | 0.78 | 0.791 | 0.752 | 0.78 | 0.764 | 0.72 | 0.429 | 0.184 | 0.124 |
| | 0.068 | 0.744 | 0.781 | 0.773 | 0.754 | 0.741 | 0.7 | 0.479 | 0.138 | 0.103 |
| | 0.108 | 0.778 | 0.781 | 0.793 | 0.79 | 0.763 | 0.732 | 0.472 | 0.181 | 0.147 |

TABLE 2-continued

| | | | | | | | | | |
|---|---|---|---|---|---|---|---|---|---|
| Average | 0.08725 | 0.771 | 0.77925 | 0.767 | 0.776 | 0.747 | 0.705 | 0.4498 | 0.17075 | 0.12275 |
| SEM | 0.00818 | 0.009 | 0.005603 | 0.01 | 0.008 | 0.011 | 0.014 | 0.0151 | 0.01095 | 0.00919 |
| A-Blank | 0 | 0.683 | 0.692 | 0.68 | 0.689 | 0.66 | 0.618 | 0.3625 | 0.0835 | 0.0355 |
| % | | 100 | 101.2806 | 99.49 | 100.8 | 96.52 | 90.45 | 53.055 | 12.221 | 5.19576 |
| SEM | | 1.295 | 0.82008 | 1.479 | 1.134 | 1.561 | 2.015 | 2.2062 | 1.60259 | 1.34456 |

Legend for Table 2:
NC: no cells; A-Blank: Average-Blank; %: [A-blank] − [A-Blank]$_{control}$/[A-Blank]$_{control}$; SEM: Standard error of the mean. Concentrations are in μM and the data are O.D. readings at 570 nm.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of inhibiting a breast cancer cell growth in a subject comprising administering to the subject an effective amount of an inhibitor selected from the group consisting of: a compound of formula II:
wherein,

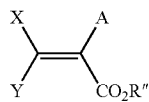
(II)

X and Y represent H, halide, or alkyl group;
A is

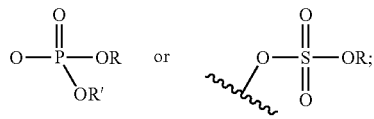

R and R' represent H, alkyl, or aryl or heteroaryl ester;
R" represents H, or alkyl, or aryl or heteroaryl ester;
any isomers or salts thereof;
with the proviso that the compound of formula II is not

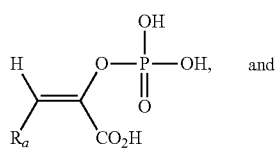

wherein R$_a$=H, (Z)—F, (Z)—Cl, (E)-Cl and (Z)—CH$_3$;

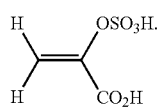

2. The method of claim 1, which further comprising administering a second chemotherapeutic agent.

3. The method of claim 2, wherein the second chemotherapeutic agent is selected from the group consisting of: altretamine, asparaginase, BCG, bleomycin sulfate, busulfan, carboplatin, carmusine, chlorambucil, cisplatin, claladribine, 2-chlorodeoxyadenosine, cyclophosphamide, cytarabine, dacarbazine imidazole carboxamide, dactinomycin, daunorubicin-dunomycin, dexamethosone, doxurubicin, docetaxol, trastuzumab, etoposide, floxuridine, fluorouracil, fluoxymesterone, flutamide, fludarabine, goserelin, hydroxyurea, idarubicin HCl, ifosfamide, interferon alfa, interferon alfa 2a, interferon alfa 2b, interferon alfa n3, irinotecan, leucovorin calcium, leuprolide, levamisole, lomustine, inegestrol, melphalan, L-sarcosylin, melphalan hydrochloride, MESNA, mechlorethamine, methotrexate, mitomycin, mitoxantrone, mercaptopurine, paclitaxel, plicamycin, prednisone, procarbazine, streptozocin, tamoxifen, 6-thioguanine, thiotepa, vinblastine, vincristine and vinorelbine tartrate.

4. The method of claim 1, wherein the effective amount of the inhibitor is delivered by direct intravenous or intraarterial injection to a tumor, or using a delivery system, or administered orally in the form of a tablet, capsule or liquid.

5. The methods of claim 1, wherein the inhibitor is delivered using a delivery system.

6. The methods of claim 2, wherein the second chemotherapeutic agent is delivered using a delivery system.

7. The method of claim 5, wherein the delivery system is selected from the group consisting of micelles, liposomes, transdermal and inhalation.

8. The method of claim 1, wherein the compound of formula II is chosen from:

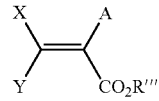
(II)

wherein,
X and Y represent H, halide, or alkyl group;
A is

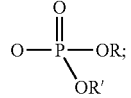

R and R' represent CH$_3$;
R" represents CH$_3$ or C$_2$H$_5$;
any isomers or salts thereof.

* * * * *